US009271749B2

(12) United States Patent
Kiapour et al.

(10) Patent No.: US 9,271,749 B2
(45) Date of Patent: Mar. 1, 2016

(54) SYSTEM AND METHOD FOR AN ARTICULATING GRASPER END-EFFECTOR

(71) Applicant: Specialty Surgical Instrumentation Inc., Antioch, TN (US)

(72) Inventors: Ali Kiapour, Providence, RI (US); Matthew J. Attar, Seekonk, MA (US)

(73) Assignee: Specialty Surgical Instrumentation Inc., Antioch, TN (US)

( * ) Notice: Subject to any disclaimer, the term of this patent is extended or adjusted under 35 U.S.C. 154(b) by 366 days.

(21) Appl. No.: 13/721,129

(22) Filed: Dec. 20, 2012

(65) Prior Publication Data
US 2013/0158593 A1 Jun. 20, 2013

Related U.S. Application Data

(60) Provisional application No. 61/578,072, filed on Dec. 20, 2011.

(51) Int. Cl.
*A61B 17/00* (2006.01)
*A61B 17/29* (2006.01)

(52) U.S. Cl.
CPC .......... *A61B 17/29* (2013.01); *A61B 2017/291* (2013.01); *A61B 2017/2927* (2013.01)

(58) Field of Classification Search
CPC ............... A61B 17/29; A61B 17/2909; A61B 2017/291; A61B 2017/292; A61B 2017/2912; A61B 2017/2913; A61B 2017/2916; A61B 2017/2926; A61B 2017/2927; A61B 2017/2929; A61B 2017/2932; A61B 2017/2933; A61B 2017/2936; A61B 17/2804; A61B 17/2812; A61B 17/2841; A61B 2017/2915; A61B 2017/2934; A61B 2017/2938

USPC ......................................................... 606/205
See application file for complete search history.

(56) References Cited

U.S. PATENT DOCUMENTS

| 5,330,502 | A | 7/1994 | Hassler et al. |
| 5,383,888 | A | 1/1995 | Zvenyatsky et al. |
| 5,391,180 | A | 2/1995 | Tovey et al. |
| 5,411,481 | A | 5/1995 | Allen et al. |
| 5,474,571 | A | 12/1995 | Lang |
| 5,490,819 | A | 2/1996 | Nicholas et al. |
| 5,514,157 | A | 5/1996 | Nicholas et al. |
| 5,607,450 | A | 3/1997 | Zvenyatsky et al. |

(Continued)

FOREIGN PATENT DOCUMENTS

WO 9814124 A1 4/1998

*Primary Examiner* — Katherine M Shi
*Assistant Examiner* — Kankindi Rwego
(74) *Attorney, Agent, or Firm* — Hayes Soloway, P.C.

(57) ABSTRACT

An endoscopic medical device system includes an elongated shaft assembly, a cam assembly and an articulating distal end assembly. The elongated shaft assembly extends along a main axis and includes first and second actuator rods arranged parallel to each other and the first actuator rod is longer than the second actuator rod. The cam assembly includes a cam, and the proximal ends of the first and second actuator rods are configured to be slidably attached to first and second locations of the cam, respectively, and the distal ends of the first and second actuator rods are positioned at the same distance from the cam center. The articulating distal end assembly extends along the main axis and is pivotally connected to the distal ends of the first and second actuator rods. Rotation of the cam around an axis perpendicular to the main axis provides angular displacement of the distal end assembly relative to the main axis.

28 Claims, 3 Drawing Sheets

(56) References Cited

U.S. PATENT DOCUMENTS

| | | |
|---|---|---|
| 5,766,205 A | 6/1998 | Zvenyatsky et al. |
| 5,782,859 A | 7/1998 | Nicholas et al. |
| 5,827,323 A * | 10/1998 | Klieman et al. ............ 606/205 |
| 5,849,022 A | 12/1998 | Sakashita et al. |
| 6,063,103 A | 5/2000 | Hashiguchi |
| 6,554,844 B2 | 4/2003 | Lee et al. |
| 2002/0177874 A1 | 11/2002 | Nicholas et al. |
| 2005/0143774 A1 | 6/2005 | Polo |
| 2006/0025809 A1 | 2/2006 | Shelton |
| 2006/0025810 A1 | 2/2006 | Shelton |
| 2006/0025812 A1 | 2/2006 | Shelton |
| 2006/0190029 A1 | 8/2006 | Wales |
| 2006/0190031 A1 | 8/2006 | Wales et al. |
| 2006/0212069 A1 | 9/2006 | Shelton |
| 2006/0229665 A1 | 10/2006 | Wales et al. |
| 2006/0259071 A1 | 11/2006 | Nicholas et al. |
| 2006/0271101 A1 | 11/2006 | Saadat et al. |
| 2007/0027468 A1 | 2/2007 | Wales et al. |
| 2007/0162072 A1 | 7/2007 | Nicholas et al. |
| 2008/0077159 A1 | 3/2008 | Madhani et al. |
| 2008/0147113 A1 | 6/2008 | Nobis et al. |
| 2008/0255607 A1 | 10/2008 | Zemlok |
| 2009/0065549 A1 | 3/2009 | Viola |
| 2009/0171354 A1 | 7/2009 | Deville et al. |
| 2010/0298864 A1 | 11/2010 | Castro |

* cited by examiner

SYSTEM AND METHOD FOR AN ARTICULATING GRASPER END-EFFECTOR

CROSS REFERENCE TO RELATED CO-PENDING APPLICATIONS

This application claims the benefit of U.S. provisional application Ser. No. 61/578,072 filed on Dec. 20, 2011 and entitled SYSTEM AND METHOD FOR AN ARTICULATING GRASPER END-EFFECTOR OF AN ENDOSCOPIC MEDICAL DEVICE which is commonly assigned and the contents of which are expressly incorporated herein by reference.

FIELD OF THE INVENTION

The present invention relates to a system and a method for an articulating grasper end-effector, and in particular, to an articulating grasper end-effector that moves angularly relative to the device's main axis

BACKGROUND OF THE INVENTION

Endoscopic medical instruments with articulating grasper jaws are used in various surgical procedures for grasping organs in a specific direction, or suturing. Prior art systems usually include grasper jaws that articulate via a cable or an actuator rod system. In most of the prior art systems the articulating grasper jaws are not held rigid in their angular position. This may result in abrasion of the tissue or organ being grasped, injury of the surrounding tissue, or ineffective suturing.

Accordingly there is a need for improved methods and systems that allow articulation of a grasper end-effector of an endoscopic medical instrument while holding the distal end in a rigid position.

SUMMARY OF THE INVENTION

The present invention provides a device having an elongated shaft with an articulating grasper end-effector that moves angularly from the main shaft axis. The articulating grasper end-effector is used to grasp tissue or an organ at an angle relative to the device's main axis or to change the orientation of the grasped organ while holding the grasper end-effector in a rigid position.

In general, in one aspect, the invention features a device system including an elongated shaft assembly, a cam assembly and an articulating distal end assembly. The elongated shaft assembly extends along a main axis and includes first and second actuator rods arranged parallel to each other and the first actuator rod is longer than the second actuator rod. The cam assembly includes a cam, and the proximal ends of the first and second actuator rods are configured to be slidably attached to first and second locations of the cam, respectively, and the distal ends of the first and second actuator rods are positioned at the same distance from the cam center. The articulating distal end assembly extends along the main axis and is pivotally connected to the distal ends of the first and second actuator rods. Rotation of the cam around an axis perpendicular to the main axis provides angular displacement of the distal end assembly relative to the main axis.

Implementations of this aspect of the invention may include one or more of the following features. Clockwise rotation of the cam around an axis perpendicular to the main axis pivots the distal end assembly upwards relative to the main axis and counter-clockwise rotation of the cam pivots the distal end assembly downwards relative to the main axis. The proximal ends of the first and second actuator rods are slidably attached to the first and second locations of the cam via first and second pins, respectively, and the first and second pins are configured to slide within first and second slots, formed in the cam, respectively. The cam has a circular shape and the first and second slots have an arcuate shape and are dimensioned to provide angular displacement of the distal end assembly relative to the main axis in a predetermined range. The cam has a circular shape and the first and second slots comprise an arcuate shape and are dimensioned to provide angular displacement of the distal end assembly relative to the main axis in the range of −45 degrees to +45 degrees. The elongated shaft assembly further includes an outer tube, and the first and second actuator rods are disposed within the outer tube. The cam includes a ratchet on a portion of the cam periphery and a trigger extending radially from the cam periphery and activation of the trigger rotates the cam around an axis perpendicular to the main axis and the ratchet is configured to lock the angular displacement of the distal end assembly relative to the main axis. The distal end assembly includes first and second components that are articulately connected to each other. The system further includes a handle assembly and the handle assembly includes a movable handle and a stationary handle and the movable handle is pivotally connected to the stationary handle. Clockwise rotation of the movable handle moves the first and second actuator rods longitudinally forwards along the main axis and causes the first and second components of the distal end assembly to pivot open. Counter-clockwise rotation of the movable handle moves the first and second actuator rods longitudinally backwards and causes the first and second components of the distal end assembly to pivot close. The cam assembly is slidably connected to the handle assembly. The system further includes a sliding bush and the cam assembly is slidably connected to the handle assembly via the sliding bush. The cam is mounted on the sliding bush and the sliding bush is positioned within a cavity formed in the stationary handle. The system further includes a link configured to connect the proximal end of the sliding bush to the top of the movable handle. The system further includes a pin supported by a spring mechanism and extending from the distal end of the sliding bush. The pin is configured to engage a ratchet formed on a portion of the periphery of the cam and thereby to lock the ratchet and the distal end assembly at different angles relative to the main axis. The articulating distal end assembly may be one of grasping jaws, grasping blades, or grasping fingers. The articulating distal end assembly is removable and/or disposable.

In general, in one aspect, the invention features a method for providing angular displacement of an articulating distal end assembly including providing an elongated shaft assembly extending along a main axis, providing a cam assembly, providing an articulating distal end, and rotating the cam around an axis perpendicular to the main axis and thereby providing angular displacement of the distal end assembly relative to the main axis. The elongated shaft assembly includes first and second actuator rods arranged parallel to each other and the first actuator rod is longer than the second actuator rod. The cam assembly includes a cam, and the proximal ends of the first and second actuator rods are configured to be slidably attached to first and second locations of the cam, respectively, and the distal ends of the first and second actuator rods are positioned at the same distance from the cam center. The articulating distal end assembly extends along the main axis and is pivotally connected to the distal ends of the first and second actuator rods.

Among the advantages of this invention may be one or more of the following. The articulating grasper end-effector provides controlled angular movement of the grasped organ relative to the main shaft axis, while maintaining the grasper end-effector in a rigid position.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views.

DETAILED DESCRIPTION OF THE INVENTION

The present invention provides a device having an elongated shaft with an articulating grasper end-effector that moves angularly from the main shaft axis. The articulating grasper end-effector is used to grasp tissue or an organ at an angle relative to the device's main axis or to change the orientation of the grasped organ while holding the grasper end-effector in a rigid position.

Figure 1:
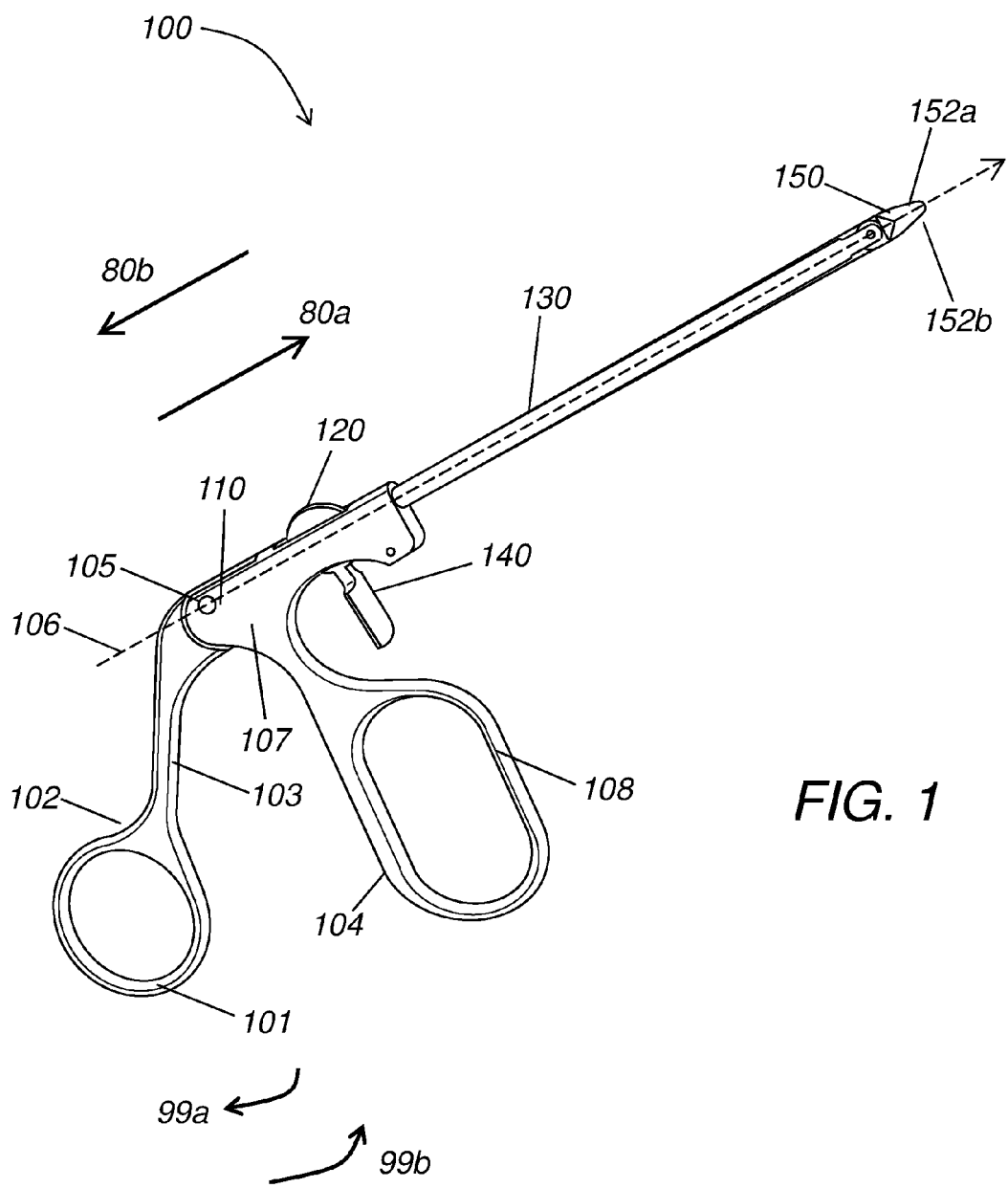
FIG. 1 is a side perspective view of an endoscopic medical device with an articulating grasper end-effector according to this invention.

Referring to FIG. 1, endoscopic medical device 100 includes a handle assembly 110, a cam assembly 120, a shaft assembly 130, and a distal end assembly 150. Handle assembly 110 includes a movable handle 102, and a stationary handle 104. Movable handle 102 includes a finger loop 101 and an arm 103 extending upward from the finger loop 102. Arm 103 is pivotally connected to stationary handle 104 and movable handle 102 pivots around pivot point 105 relative to the stationary handle 104. Stationary handle 104 includes an upper body 107 and a finger loop 108. Cam assembly 120 is integrated within a cavity formed in the upper body 107 of the stationary handle 104. Distal end assembly 150 includes two grasping jaws 152a, 152b that are articulately connected to each other and are configured to open and close via the movement of the movable handle 102, as will be described below.

Figure 2:
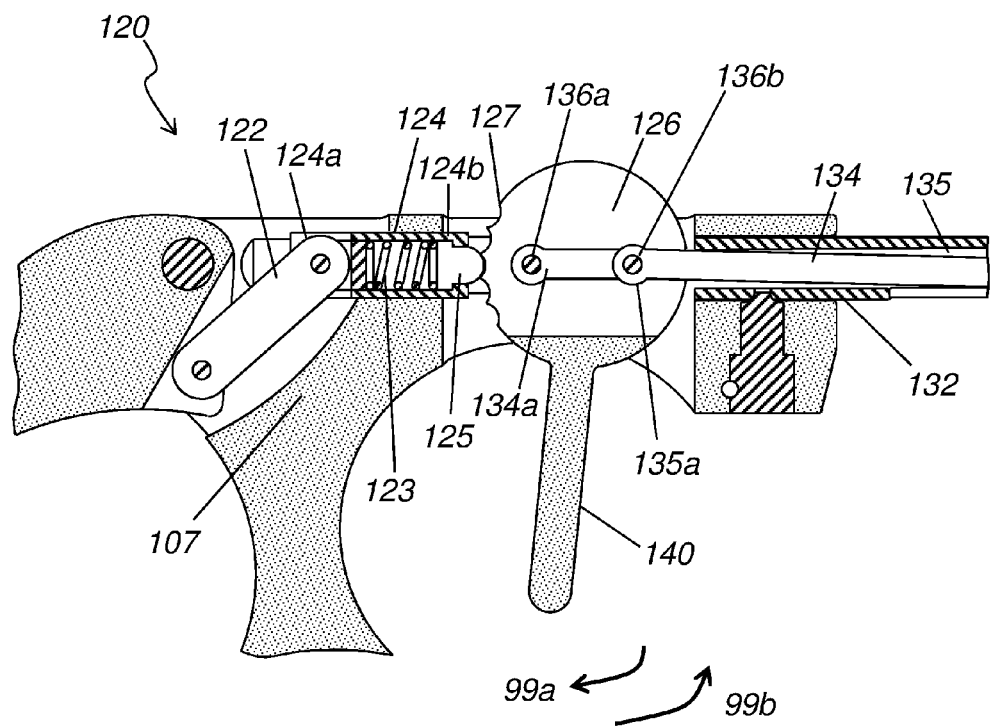
FIG. 2 is a cross-sectional view of the articulating mechanism of the device of FIG. 1.
Figure 3A:
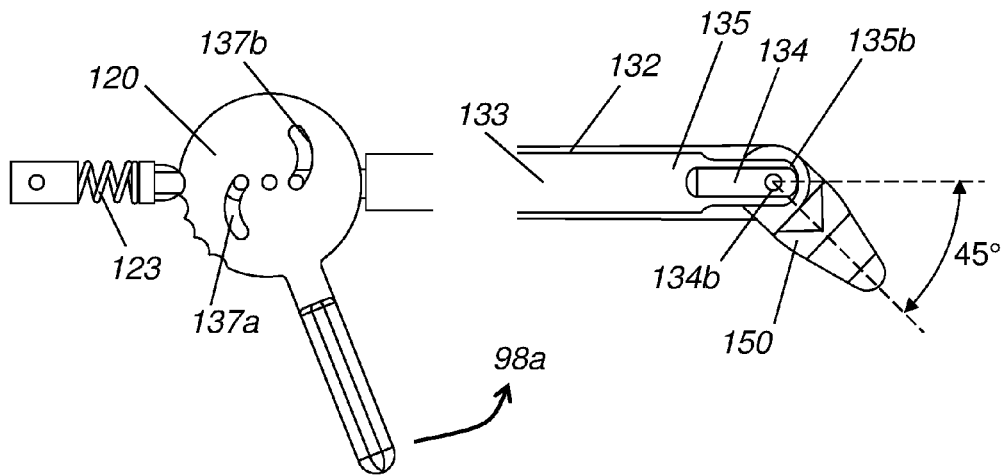
FIG. 3A is a side view of the articulating mechanism of the device of FIG. 1 depicting the grasper end-effector pointing down at 45 degrees off the main device axis.
Figure 3B:
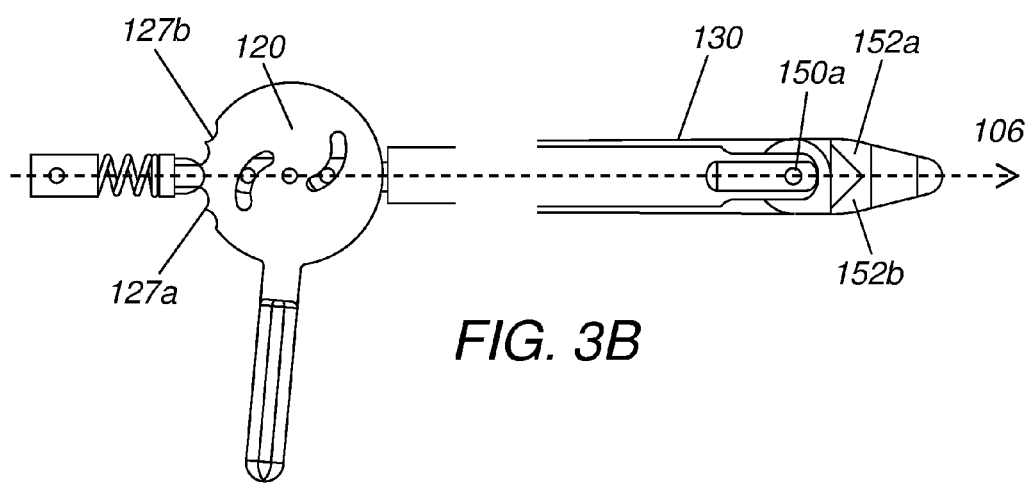
FIG. 3B is a side view of the articulating mechanism of the device of FIG. 1 depicting the grasper end-effector pointing straight at zero degrees off the main device axis.
Figure 3C:
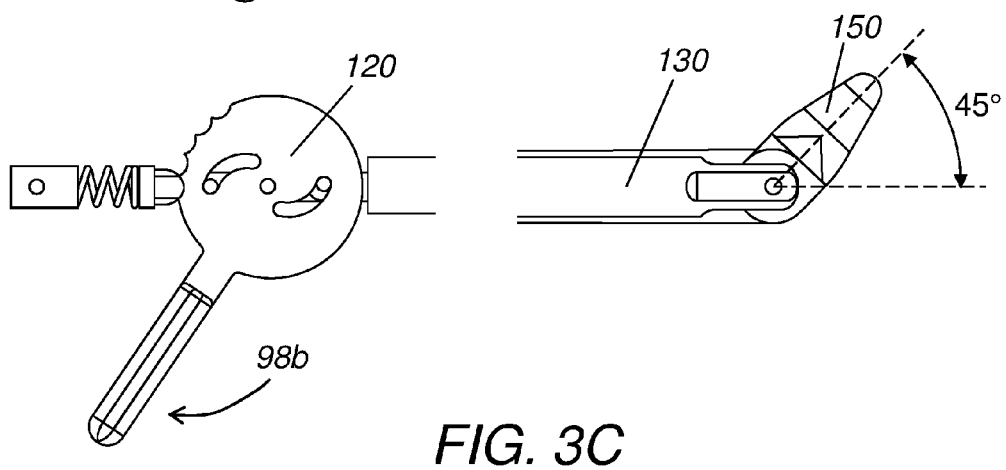
FIG. 3C is a side view of the articulating mechanism of the device of FIG. 1 depicting the grasper end-effector pointing up at 45 degrees off the main device axis.

Referring to FIG. 2, cam assembly 120 includes a circular shaped cam 126 having a ratchet 127 on a portion of its periphery. Ratchet 127 includes teeth 127a alternating with grooves 127b, shown in FIG. 3B. Cam 126 also includes a cam trigger 140 extending from its periphery. Cam 126 is mounted on a sliding bush 124 that is placed within a cylindrical opening in the upper body 107 of the stationary handle 104. A link 122 connects the proximal end of bush 124 to the top end of arm 103 of movable handle 102. Manipulation of the movable handle 102 along rotational direction 99a causes the bush 124 to slide forward along direction 80a and moves the cam 126 and the attached actuators 134, 135 forward along direction 80a and thereby opens the grasping jaws 152a, 152b of the distal assembly 150. Manipulation of the movable handle 102 along rotational direction 99b causes the bush 124 to slide backward along direction 80b and moves the cam 126 and the attached actuators 134, 135 backward along direction 80b and thereby closes the grasping jaws 152a, 152b of the distal assembly 150. Manipulation of the cam trigger 140 along rotational direction 98a moves the distal assembly 150 downward at an angle of 45 degrees relative to the main shaft axis 106, as shown in FIG. 3A. Manipulation of the cam trigger 140 along rotational direction 98b moves the distal assembly 150 upward at an angle of 45 degrees relative to the main shaft axis 106, as shown in FIG. 3C. When the cam trigger 140 is centered in a perpendicular orientation relative to the main shaft axis 106, the distal assembly 150 is aligned with the main shaft axis 106. A pin 125 supported by a spring mechanism 123 extends from the distal end 124b of bush 124 and engages the ratchet mechanism 127 to lock the ratchet 127 at different angles relative to the main shaft axis 106. This angular locking of the ratchet 127 locks the distal assembly 150 at different angles relative to the main shaft axis 106. The spacing of the ratchet teeth 127a and the ratchet groves 127b determines the angular steps within the angular range of −45 degrees to +45 degrees.

Shaft assembly 130 includes a tubular outer shaft 132 forming a cylindrical inner opening 133 and two actuators 134, 135 extending through the cylindrical inner opening 133 of the outer shaft 132. Actuators 134, 135 are arranged parallel to each other and have proximal ends 134a, 135a that are attached to cam 126 via pins 136a, 136b, respectively, and distal ends 134b, 135b that are pivotally attached to the distal end assembly 150 at the pivot point 150a, as shown in FIGS. 3A, 3B and 3C. Actuator rod 134 is longer than actuator rod 135. Pins 136a, 136b slide inside slots 137a, 137b formed on cam 126, shown in FIG. 3A. Slots 137a, 137b have an arcuate shape and are dimensioned to provide angular displacements of the grasper jaw assembly in the range of −45 degrees to +45 degrees (total range of 90 degrees), as shown in FIG. 3A and FIG. 3C.

In operation, moving the movable handle along rotational directions 99a, 99b moves the actuators 134, 135 forward and backward and opens or closes the grasping jaws 152a, 152b, respectively. Moving the cam trigger 140 along rotational directions 98a, 98b slides the proximal ends 134a, 135a of actuators 134, 135 within cam slots 137a, 137b and moves the distal end assembly 150 downward or upward at an angle relative to the shaft main axis 106, as shown in FIG. 3a and FIG. 3C, respectively.

The present invention is applicable to various grasping end assemblies including grasping jaw assemblies, grasping blade assemblies, grasping finger assemblies, among others. The grasping jaw assemblies are removable and can be interchanged. In some embodiments, the grasping jaw assemblies are disposable. The invention provides a significant cost reduction in the overall medical device. The articulating mechanism of the present invention allows the replacement of multiple sets of instruments having grasping jaw assemblies at fixed angles. The angular articulation of the jaw assemblies provides more flexibility in the angular positioning of the device through narrow incisions during minimally invasive surgery. Furthermore, the articulating mechanism of the present invention has fewer moving parts and reduces the complexity of the articulating jaw mechanisms of the prior art.

Several embodiments of the present invention have been described. Nevertheless, it will be understood that various modifications may be made without departing from the spirit and scope of the invention. Accordingly, other embodiments are within the scope of the following claims.

What is claimed is:

1. A device system comprising:
an elongated shaft assembly extending along a main axis and comprising first and second actuator rods arranged parallel to each other and wherein said first actuator rod is longer than said second actuator rod;
a cam assembly comprising a cam, and wherein the proximal ends of the first and second actuator rods are configured to be slidably attached to first and second locations of said cam, respectively, and the distal ends of the first and second actuator rods are positioned at the same distance from the cam center;
an articulating distal end assembly extending along the main axis and being pivotally connected to the distal ends of the first and second actuator rods; and
wherein rotation of the cam around an axis perpendicular to the main axis provides angular displacement of the distal end assembly relative to the main axis; and
wherein the proximal ends of the first and second actuator rods are slidably attached to the first and second locations of said cam via first and second pins, respectively, and wherein said first and second pins are configured to slide within first and second slots, formed in the cam, respectively.

2. The system of claim 1 wherein clockwise rotation of the cam around an axis perpendicular to the main axis pivots the distal end assembly upwards relative to the main axis and counter-clockwise rotation of the cam pivots the distal end assembly downwards relative to the main axis.

3. The system of claim 1, wherein said cam comprises a circular shape and wherein said first and second slots comprise an arcuate shape and are dimensioned to provide angular displacement of the distal end assembly relative to the main axis in a predetermined range.

4. The system of claim 1, wherein said cam comprises a circular shape and wherein said first and second slots comprise an arcuate shape and are dimensioned to provide angular displacement of the distal end assembly relative to the main axis in the range of −45 degrees to +45 degrees.

5. The system of claim 1, wherein the elongated shaft assembly further comprises an outer tube, and said first and second actuator rods are disposed within the outer tube.

6. The system of claim 1, wherein the cam comprises a ratchet on a portion of the cam periphery and a trigger extending radially from the cam periphery and wherein activation of the trigger rotates the cam around an axis perpendicular to the main axis and the ratchet is configured to lock the angular displacement of the distal end assembly relative to the main axis.

7. The system of claim 1, wherein the distal end assembly comprises first and second components that are articulately connected to each other.

8. The system of claim 7, further comprising a handle assembly and wherein the handle assembly comprises a movable handle and a stationary handle and wherein the movable handle is pivotally connected to the stationary handle and wherein clockwise rotation of the movable handle moves the first and second actuator rods longitudinally forwards along the main axis and causes the first and second components of the distal end assembly to pivot open and wherein counter-clockwise rotation of the movable handle moves the first and second actuator rods longitudinally backwards and causes the first and second components of the distal end assembly to pivot close.

9. The system of claim 8, wherein the cam assembly is slidably connected to the handle assembly.

10. The system of claim 9, further comprising a sliding bush and wherein the cam assembly is slidably connected to the handle assembly via the sliding bush and wherein the cam is mounted on the sliding bush and the sliding bush is positioned within a cavity formed in the stationary handle.

11. The system of claim 10, further comprising a link configured to connect the proximal end of the sliding bush to the top of the movable handle.

12. The system of claim 10, further comprising a pin supported by a spring mechanism and extending from the distal end of the sliding bush and wherein said pin is configured to engage a ratchet formed on a portion of the periphery of the cam and thereby to lock the ratchet and the distal end assembly at different angles relative to the main axis.

13. The system of claim 1, wherein the articulating distal end assembly comprises one of grasping jaws, grasping blades, or grasping fingers.

14. The system of claim 1, wherein the articulating distal end assembly is removable and/or disposable.

15. A method for providing angular displacement of an articulating distal end assembly comprising:
providing an elongated shaft assembly extending along a main axis and comprising first and second actuator rods arranged parallel to each other and wherein said first actuator rod is longer than said second actuator rod;
providing a cam assembly comprising a cam, and wherein the proximal ends of the first and second actuator rods are configured to be slidably attached to first and second locations of said cam, respectively, and the distal ends of the first and second actuator rods are positioned at the same distance from the cam center;
providing an articulating distal end assembly extending along the main axis and being pivotally connected to the distal ends of the first and second actuator rods; and
rotating the cam around an axis perpendicular to the main axis and thereby providing angular displacement of the distal end assembly relative to the main axis; and
wherein the proximal ends of the first and second actuator rods are slidably attached to the first and second locations of said cam via first and second pins, respectively, and wherein said first and second pins are configured to slide within first and second slots, formed in the cam, respectively.

16. The method of claim 15, wherein clockwise rotation of the cam around an axis perpendicular to the main axis pivots the distal end assembly upwards relative to the main axis and counter-clockwise rotation of the cam pivots the distal end assembly downwards relative to the main axis.

17. The method of claim 15, wherein said cam comprises a circular shape and wherein said first and second slots comprise an arcuate shape and are dimensioned to provide angular displacement of the distal end assembly relative to the main axis in a predetermined range.

18. The method of claim 15, wherein said cam comprises a circular shape and wherein said first and second slots comprise an arcuate shape and are dimensioned to provide angular displacement of the distal end assembly relative to the main axis in the range of −45 degrees to +45 degrees.

19. The method of claim 15, wherein the elongated shaft assembly further comprises an outer tube, and said first and second actuator rods are disposed within the outer tube.

20. The method of claim 15, wherein the cam comprises a ratchet on a portion of the cam periphery and a trigger extending radially from the cam periphery and wherein activation of the trigger rotates the cam around an axis perpendicular to the main axis and the ratchet is configured to lock the angular displacement of the distal end assembly relative to the main axis.

21. The method of claim 15, wherein the distal end assembly comprises first and second components that are articulately connected to each other.

22. The method of claim 21, further comprising providing a handle assembly and wherein the handle assembly comprises a movable handle and a stationary handle and wherein the movable handle is pivotally connected to the stationary handle and wherein clockwise rotation of the movable handle moves the first and second actuator rods longitudinally forwards along the main axis and causes the first and second components of the distal end assembly to pivot open and wherein counter-clockwise rotation of the movable handle moves the first and second actuator rods longitudinally backwards and causes the first and second components of the distal end assembly to pivot close.

23. The method of claim 22, wherein the cam assembly is slidably connected to the handle assembly.

24. The method of claim 23, further comprising providing a sliding bush and wherein the cam assembly is slidably connected to the handle assembly via the sliding bush and wherein the cam is mounted on the sliding bush and the sliding bush is positioned within a cavity formed in the stationary handle.

25. The method of claim 24, further comprising providing a link configured to connect the proximal end of the sliding bush to the top of the movable handle.

26. The method of claim 24, further comprising providing a pin supported by a spring mechanism and extending from the distal end of the sliding bush and wherein said pin is configured to engage a ratchet formed on a portion of the periphery of the cam and thereby to lock the ratchet and the distal end assembly at different angles relative to the main axis.

27. The method of claim 15, wherein the articulating distal end assembly comprises one of grasping jaws, grasping blades, or grasping fingers.

28. The method of claim 15, wherein the articulating distal end assembly is removable and/or disposable.

* * * * *